(12) United States Patent
Doona et al.

(10) Patent No.: US 8,366,961 B2
(45) Date of Patent: Feb. 5, 2013

(54) CHEMICAL COMBINATION FOR THE GENERATION OF DISINFECTANT AND HEAT

(75) Inventors: Christopher J. Doona, Marlborough, MA (US); Maria Agudelo Curtin, Easton, MA (US); Irwin A. Taub, Ashland, MA (US); Kenneth Kustin, San Diego, CA (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 127 days.

(21) Appl. No.: 12/977,133

(22) Filed: Dec. 23, 2010

(65) Prior Publication Data

US 2011/0180754 A1 Jul. 28, 2011

Related U.S. Application Data

(63) Continuation of application No. 10/988,442, filed on Nov. 10, 2004, now Pat. No. 7,883,640.

(51) Int. Cl.
*C01B 11/10* (2006.01)
*C01B 11/14* (2006.01)
*A62D 3/30* (2007.01)

(52) U.S. Cl. ............. 252/187.1; 252/187.2; 252/187.21; 252/187.23; 252/187.31; 252/186.28

(58) Field of Classification Search ............... 252/187.1, 252/187.31, 187.2
See application file for complete search history.

(56) References Cited

FOREIGN PATENT DOCUMENTS
EP 196075 A2 * 10/1986

* cited by examiner

*Primary Examiner* — Peter F Godenschwager
(74) *Attorney, Agent, or Firm* — Roger C. Phillips

(57) ABSTRACT

This invention comprises a lightweight, portable chemical combination of reagents for sterilizing or disinfecting objects in the absence of electrical power or fire. The chemical combination includes a chemical oxidant with the capacity to liberate a biocidal intermediate, a chemical reductant of the oxidant with the capacity to react with the oxidant, and an effector to induce a reaction between the oxidant and reductant. In one embodiment, the oxidant comprises chlorite, the reductant comprises sulfite, and the effector comprises ascorbate. In another embodiment, the chemical combination comprises the oxidant, reductant, effector and iron-activated magnesium. When water or water solutions are added to either embodiment, the chemical combination generates heat, steam and a biocidal intermediate that can destroy contaminating microorganisms. In one embodiment, the biocidal intermediate is a halogen-based biocidal intermediate, such as chlorine dioxide. In another embodiment, the biocidal intermediate is a halogen-free biocidal intermediate.

11 Claims, 1 Drawing Sheet

CHEMICAL COMBINATION FOR THE GENERATION OF DISINFECTANT AND HEAT

CROSS REFERENCE TO RELATED APPLICATION

This application is a continuation of U.S. patent application Ser. No. 10/988,442, filed Nov. 10, 2004, entitled "Chemical Combination for the Generation of Disinfectant and Heat", now U.S. Pat. No. 7,883,640.

STATEMENT OF GOVERNMENT INTEREST

The invention described herein may be manufactured and used by the U.S. Government for Governmental purposes without the payment of any royalty thereon.

BACKGROUND OF THE INVENTION

1. Field of the Invention

The present invention generally relates to a safe, portable chemical combination of reagents which, when combined, requires no external power sources to conveniently and safely generate heat, steam and a biocidal chemical agent that destroys contaminating microorganisms or chemical agents on contaminated objects or surfaces. The present invention does not require external sources of power such as electricity or fire.

2. Description of Related Art

Microbial contamination of objects and surfaces such as food contact surfaces and food service equipment in kitchen environments (e.g., cutting boards, knives, and utensils), of military clothing, vehicles, and equipment, and of medical, dental, or veterinary instruments can lead to the transmission of infectious pathogens and the spread of food-borne illnesses and other diseases. Inactivating these pathogenic microorganisms to prevent infection and the spread of disease requires disinfection or sterilization through the application of a lethal treatment of commensurate stringency.

Military activities in remote or open field locations often experience conditions wherein electrical power, water, or fire is unavailable, of limited availability, or undesirable in such environments. Military surgical teams in such instances require clean, safe, sterile instruments and equipment that contact the patient. While pre-packaged instruments transported to these locations arrive initially sterile, they become contaminated following their use in medical procedures. It is absolutely necessary that these contaminated instruments be cleaned and sterilized before subsequent use with additional patients to prevent the transmission of infection and disease.

In representative hospitals, clinics, and laboratories, contaminated instruments are customarily washed, scrubbed, sealed in germ-free packaging, and then sterilized in an autoclave for re-use. Typically, pressurized steam autoclaves powered by electrical power generate heat and/or steam as the agents most frequently used to sterilize glass, metal, or high-melting plastic tools and instruments. However, it is currently not possible to carry out such sterilization techniques in military facilities located in remote or open field environments where large pressurized steam autoclaves are not available, and wherein electrical power, water, or fire is unavailable, of limited availability, or undesirable. The challenge of replenishing the supply of available sterile instruments in these circumstances often requires transporting contaminated equipment via aircraft to distant hospitals with the facilities to support the operation of a pressurized steam autoclave. In order to safely and effectively sterilize contaminated surgical instruments for immediate re-use on site in these remote or difficult-to-access locations with limited power supplies, it is necessary to consider alternatives to electrical- or fossil fuel-powered sterilization using autoclaves.

There are several prior art sterilization methods used to sterilize objects such as field feeding equipment, military equipment, or surgical tools. However, such prior art methods are not suited for remote, field environments such as those typically found in military situations or in countries ravaged by disease and famine wherein international health workers and doctors conduct medical operations in situ. The most widely used chemical disinfectants are halogens, ozone, chlorine dioxide, chloramines, and ethylene oxide. Among them, the most effective disinfectant is chlorine. Ozone and chlorine dioxide are very close to chlorine with respect to effectiveness. Other halogens, such as bromine and iodine, are less effective as is ethylene oxide, although, under certain circumstances, one of these agents may be recommended over the others. For example, ethylene oxide is frequently used to fumigate textiles because ethylene oxide is readily decomposed to non-toxic products on contact with air.

The major disadvantages of the two most effective chemical disinfectants, i.e. chlorine and ozone, are problems related to their storage, transport, and generation. Chlorine is stored as a gas in heavy pressurized cylinders. Ozone is unstable, and is generated in situ, which requires a source of electricity. Heavy equipment is typically involved whether electrical power is obtained from batteries or generators. Ozone, moreover, is usually generated in an electrochemical cell which must be continuously supplied with air at one electrode and water at the other electrode thereby necessitating the use of further mechanical and/or electrical implements and devices. Other halogens and traditional disinfectants, such as hydrogen peroxide, chloramines, and ethylene oxide, are unstable, not sufficiently effective, or difficult to handle.

Another technique for sterilizing or disinfecting objects entails the use of the disinfectant Super Tropical Bleach (sodium hypochlorite in aqueous solution). This bleach is typically used to decontaminate military equipment, vehicles, weapons, clothing, and field-kitchen equipment. However, hypochlorite cannot be generated on-site and must be transported and stored in large, heavy containers. Hypochlorite is also caustic and difficult to ship due to its potential health hazards. Furthermore, hypochlorite is especially corrosive to metal surfaces such as those found on military equipment, vehicles, weapons systems, and generators. Additionally, hypochlorite disinfection produces environmentally hazardous by-products including carcinogenic compounds that endanger human health. The disadvantages of Super Tropical Bleach prevent its use in disinfecting contaminated surgical instruments in remote or far-forward environments.

The use of radiation to achieve disinfection and sterilization also has many disadvantages. Whether the radiation takes the form of ultraviolet light, X-rays, or nuclear emissions, it is usually applied in an enclosed environment. The generation of such high-energy radiation either involves electricity, for ultraviolet light and X-rays, or lead-lined containers and special handling, in the case of shielded installations for radioactive nuclides. Factors such as high power, heavy and complex equipment, and the necessity of extreme safety precautions preclude the rapid deployment of radiation sources from one location to another, especially in remote areas.

Thus, these aforesaid sterilization and disinfection methods that use chemicals or radiation are not suitable for remote, field operations and in situations wherein electrical power is not available or of limited availability.

Another known sterilization and disinfection technique involves chlorine dioxide synthesis. Known chlorine dioxide synthesis techniques typically use one of three methods: (a) electrochemical, (b) acidification, and (c) oxidation. Each of these three methods is described in the ensuing description.

a) Electrochemical Methods

The electrochemical methods involve the formation of chlorine dioxide from chlorine-containing compounds of lower chlorine oxidation number, such as, but not limited to, chloride, hypochlorite, or chlorite ions, by passage of an electrical current through solutions of these electrolytes in an electrochemical cell. For example, Tremblay Patent Application Publication No. U.S. 2003/0006144 discloses an electrochemical method that requires the production of relatively large volumes of electrolyte that must be constantly stirred and transported in small amounts using an electrochemical cell. The electrochemical cell typically comprises liquid reservoirs, pumps, and batteries which are not only heavy, voluminous and bulky, but also are difficult to operate without a source of electricity or fire. Furthermore, although potable drinking water can be produced from such an electrochemical cell, Herrington U.S. Pat. No. 6,736,966 do not disclose achievement of sterilization, the more rigorous state of complete elimination of microorganisms.

b) Acidification

Acidification involves the formation of chlorine dioxide by proton transfer to chlorite ion. The chlorous acid so produced disproportionates to yield chloride and chlorate ions, and various amounts of chlorine dioxide. Kampa Patent Application Publication No. U.S. 2004/0062680 ("Kampa") discloses an apparatus and method wherein the components needed for reaction are sequestered into two compartments separated by a rupturable membrane. This method can be used for acidification if a component in one compartment is a proton-releasing reagent, and the other component in the second compartment is a chlorite salt. Such a technique is prone to several problems the solutions of which make the techniques disclosed in Kampa undesirable for field sterilization. For example, the acidification reactions may be too slow and require expensive catalysts that do not last long as is found in Ostgard U.S. Pat. No. 6,399,039. Barenberg et al. U.S. Pat. No. 5,980,826 ("Barenberg") discloses a chemical combination which is a variation on the acidification method and uses a hydrophobic material to contact a contaminated surface, a hydrophilic material to introduce water needed to release protons, a proton-releasing reagent and a chlorite salt. However, the chemical combination described in Barenberg requires bulky material and precise control in order to achieve the correct amount of moisture in the atmosphere. Thus, the technique described in the aforesaid Barenberg patent is not suited to the rigorous sterilization requirements associated with remote field operations as is frequently found in military applications (e.g., high altitudes or desert climates). Klatte U.S. Pat. No. 6,645,320 describes a technique involving the use of a zeolite to store the proton-releasing compound and chlorite salt in a mixed, but unreactive state. However, such a technique uses costly materials, requires fluid flow methodologies, and is not suited to the sterilization requirements associated with remote sites wherein electrical power is not available.

c) Oxidation

Oxidation methods require the formation of chlorine dioxide by using a chemical oxidant to raise the oxidation number of a chlorine-containing chemical such as sodium chlorite. A widely used oxidant is chlorine gas, which must be transported to the site in a heavy pressurized gas cylinder. In addition, there are problems in gas delivery which require considerable heavy, energy-consuming equipment to make the device effective as a biocide. Such a technique is disclosed in Jefferis, III et al. U.S. Pat. No. 4,908,188.

Thus, as shown above, none of these aforementioned chlorine dioxide synthesis methods provide a safe, convenient, reliable means for generating sufficient chlorine dioxide to achieve sterilization of objects in a relatively short time and in remote locations.

There are also disinfection methods and techniques that do not use chlorine dioxide. Such a method is described in Tarancon U.S. Pat. No. 5,229,072. This technique uses a fluorine-containing interhalogen compound such as gaseous chlorine trifluoride which hydrolyzes upon contact with liquid water or gaseous water vapor to release biocidal products. This technique necessitates the safe handling of corrosive and expensive materials as well as toxic gases. Furthermore, this technique requires a chamber of controlled humidity to effectuate disinfection. Thus, this technique is not suited for remote field operations.

There are other prior art techniques and methods that are variations of the techniques and methods described in the foregoing description. For example, Rosenblatt et al. U.S. Pat. No. 4,504,442 also discloses the use of chlorine dioxide gas as a chemosterilizing agent. Contaminated surfaces are contacted with an effective amount of gaseous chlorine dioxide for a predetermined amount of time to kill bacterial spores at a temperature that does not overly exceed ambient temperature. Rosenblatt et al U.S. Pat. No. 4,681,739 discloses the use of chlorine dioxide gas as a chemosterilizing agent. The method comprises the step of exposing a surface contaminated with spores to a humid gaseous environment and then exposing the spores to an amount of gaseous chlorine dioxide. Drake U.S. Pat. No. 6,042,802 discloses a method and apparatus for generating and using chlorine dioxide. Specifically, this patent teaches a method for generating a volume of disinfectant/sterilant fluid having a predetermined concentration of chlorine dioxide. The method includes transferring the generated chlorine dioxide gas to a separate disinfectant chamber containing a liquid solvent. The liquid solvent is chosen from the group consisting of water, alcohol, organic solvents and chlorinated solvents.

Aoyagi U.S. Patent Application No. U.S. 2003/0136426 discloses a method for cleaning and sterilizing medical devices. The medical devices are immersed in a chlorine dioxide solution. Thereafter, the medical device is placed in a chlorine dioxide gas atmosphere. Nelson et al. Patent Application Publication No. U.S. 2004/0101438 discloses a method and apparatus for sterilizing or sanitizing a container for food. Chlorine gas is produced either inside or outside the container and then circulated inside and throughout the container. The chlorine gas is then removed from the container and is reclaimed by dissolving it in a solvent. However, the foregoing techniques and methods suffer from one or more of the drawbacks and disadvantages described in the foregoing description (i.e. complex, bulky and expensive equipment, equipment that requires electrical power, etc.) and therefore, are not suited for use in remote locations wherein electrical power is not available or of limited availability, or wherein fire is either not available or undesirable.

Thus, it is apparent that currently, there is no portable, power-free method to safely, conveniently, and controllably generate sterilant or disinfectant in field environments, particularly in remote locations, that can be used to sanitize field feeding equipment, decontaminate military clothing or equipment, or sterilize medical instruments. With respect to sterilizing contaminated medical or surgical instruments, there is currently no alternative to the costly and inconvenient practice of collecting the used medical or surgical instruments and tools, removing them from the remote field environment, transporting them to a distant site where they are sterilized in electrically-powered hospital steam autoclaves, packaged, and then transported back to the remote field environment for reuse. What is needed is a technique whose precursors can be safely and readily transported to field locations (including difficult-to-access environments or remote locations) and that requires no external power sources to controllably and safely generate a lethal biocidal chemical agent to sterilize objects or surfaces (e.g. field feeding equipment, medical instruments, military clothing or equipment, etc.) on site so that such objects can be cleaned, sterilized, and reused quickly and safely.

SUMMARY OF THE INVENTION

The present invention is directed towards portable and power-free sterilization or disinfection of contaminating microorganisms through the use of chemical energy in the form of a chemical combination of safe, dry reagents that mix in water to produce a biocidal chemical agent, heat, and humidity. The atmosphere thus created is sufficiently lethal to destroy contaminating microorganisms, biological agents or bio-threats to human health such as viruses, parasites and oocysts, bacteria and spores that cause food-borne illness, infection, or disease. The chemical combination of the present invention is specifically configured for use in situations where autoclave facilities are unavailable or remote, where electricity or fire are not available, or the use of fire is dangerous or otherwise disadvantageous, or the availability or accessibility of electrical power and water is limited.

The chemical combination of the present invention concomitantly produces biocidal chemical agent, heat, and humidity. The present invention is specifically configured to sanitize, disinfect, decontaminate, or sterilize field feeding equipment, utensils, food service countertops, cutting boards, knives, utensils, food contact surfaces, military equipment, vehicles, weapons, and clothing, and surgical instruments, dental instruments, metal or high-melting plastic tools and devices. Tests and experiments have shown that after exposure to the conditions of heat, humidity, and the biocidal chemical agent acting in concert, the contaminating microorganisms show no detectable formation of colonies when recovered on appropriate media. The chemical combination of the present invention is also configured to take place safely in plastic containers, rubber containers, aluminum or stainless-steel containers, and autoclaves to heat, disinfect, or sterilize objects.

In one embodiment, the chemical combination of the present invention comprises constituents that can be varied in appropriate quantities or relative proportions. Specifically, this chemical combination comprises water or an aqueous solution, a chemical oxidant having the capacity to liberate a biocidal intermediate, a chemical reductant having the capacity to reduce the chemical oxidant, an effector that interacts with the chemical oxidant releasing biocide and inducing chemical reaction between the chemical oxidant and the chemical reductant, and a metallic reductant that has the capacity to controllably reduce water or an aqueous solution.

In another embodiment, the chemical combination of the present invention generates combinations of heat, humidity or steam, and a biocidal chemical agent that decontaminates, disinfects, or sterilizes objects or surfaces contaminated with target microorganisms, but does not use a metallic reductant. In such an embodiment, the chemical combination of the present invention comprises water or aqueous solution, a chemical oxidant with the capacity to liberate a biocidal chemical agent through chemical reaction, a chemical reductant having the capacity to reduce said chemical oxidant, and an effector that liberates the biocidal chemical agent and induces further chemical reaction between the chemical oxidant and the chemical reductant. Preferably, the chemical oxidant is sodium chlorite, the chemical reductant is sodium sulfite, and the effector is sodium hydrogen ascorbate. The resulting aqueous chemical reaction is exothermic. Thus, it releases thermal energy thereby increasing the temperature and the relative humidity of the surrounding atmosphere. Upon addition of the water or water solutions, the ascorbate-initiated reduction of chlorite begins with the transfer of an electron from chlorite to ascorbate that causes a release of heat, a decrease in the solution pH, and the release of chlorine dioxide in both heated gaseous and aqueous forms. After initiation by ascorbate, chemical reaction intermediates generated by the ascorbate-chlorite initial reaction induce chemical reaction between the oxidant chlorite and the reductant sulfite, which produces heat and increase the solution pH. The resulting heated chlorine dioxide is a lethal biocidal agent as either a heated gaseous and/or aqueous solution. Carrying out this aspect of the present invention inside a closed container can maintain an atmosphere of biocidal chemical agent, heat, and humidity for a time sufficient to effect the destruction of all contaminating microorganisms present.

The heat generated by the chemical reaction of these constituents can be sufficient to boil water, thereby bathing the objects to be disinfected or sterilized in an atmosphere of moist heat containing a biocidal chemical agent. The final products yielded by the chemical combination of the present invention are environmentally benign dehydroascorbic acid, carbon dioxide, sodium chloride, sodium sulfate, and chlorine dioxide.

In the preferred embodiment, the chemical effector is chosen from the group of protonated ascorbate-species consisting of hydrogen ascorbate ion, ascorbic acid, and ascorbate dianion. In other embodiments, the effector can be other chemical compounds, such as reducing sugars, or other organic acids, such as erythorbic acid or tartaric acid and their respective ions.

In one embodiment of the chemical combination of the present invention, chlorite is used as the chemical oxidant to generate the biocidal chemical agent chlorine dioxide. In another embodiment, the chemical combination of the present invention contains a chemical oxidant that does not contain chlorine. This particular chemical oxidant can be used in addition to, or in place of chlorite, which is the preferred oxidant. For example, the chemically similar halogen-containing oxidant bromate could be used. Additional oxidants could include other halogen-containing species such as hypobromite or bromite, and halogen-free species such as persulfate, or hydrogen peroxide. In these embodiments, the exposure of the chemical oxidant to the effector, such as ascorbate, produces reactive potential or actual biocidal agents such as bromine dioxide, sulfate radical ion, or hydroxyl radical, respectively.

In a preferred embodiment, the chemical combination of the present invention uses chlorite as the chemical oxidant and sulfite as the chemical reductant. It is possible to construct other embodiments with chlorite, in which the reductant is some other reducing species such as, but not limited to, hypophosphorus acid or phosphorus acid. These additional reductants can be used in further embodiments incorporating other halogen-based or non-halogen-based oxidants.

In another embodiment, the present invention is directed to a chemical combination that generates copious and sustainable amounts of heat, humidity or steam, and a biocidal chemical agent that decontaminates, disinfects, or sterilizes objects or surfaces contaminated with target microorganisms. In this embodiment, the chemical combination comprises water or water solutions, a chemical oxidant having the capacity to liberate a biocidal intermediate, a chemical reductant having the capacity to reduce the chemical oxidant, and effector that interacts with the chemical oxidant to release biocide and induce chemical reaction between the chemical oxidant and the chemical reductant, and a metallic reductant blended with an activator. The combination of the metallic reductant blended with the activator has the capacity to controllably reduce water or aqueous solutions. Preferably, in this embodiment, the chemical oxidant is sodium chlorite, the chemical reductant is sodium sulfite, the effector is sodium hydrogen ascorbate, and the metallic reductant is magnesium blended with 5 mole percent iron, and referred to hereinafter as Mg(Fe). These aforementioned constituents are mixed in a single reactor vessel. Preferably, the dry components of the chemical combination are first added together. Chemical reactions do not occur until after the addition of water or water solutions. Upon mixing the dry constituents with water, exothermic magnesium reduction of water to dihydrogen occurs. At approximately the same time, chlorine dioxide is released as ascorbate reacts with chlorite.

In an alternate embodiment, the oxidant, e.g. chlorite, is first dissolved in water, and the remaining dry constituents, the chemical oxidant, effector and metallic reductant, are then added to the aqueous solution comprised of water or water solutions and the chlorite chemical oxidant. This embodiment will reduce the output of dihydrogen as the magnesium will reduce both water and dissolved chlorite. As in the magnesium-free aspect of the invention, further embodiments are possible, wherein the chemical oxidant, chemical reductant, and effector are replaced by other compounds such as those listed above in the foregoing description.

When all the aforementioned constituents of the chemical combination of the present invention have been associated in a suitable container, this chemical combination generates sustainable heat, humidity or steam, and a biocidal chemical agent that destroys contaminating microorganisms capable of inhabiting feeding equipment, food utensils, and food contact surfaces, military equipment, vehicles, and clothing; or used surgical instruments or medical equipment.

The heat generated by the chemical reaction of these constituents can be sufficient to boil water, thereby bathing the objects to be disinfected or sterilized in an atmosphere of moist heat containing a biocidal chemical agent. The final products yielded by the chemical combination of the present invention are environmentally benign magnesium hydroxide, dehydroascorbic acid, carbon dioxide, sodium chloride, sodium sulfate, and chlorine dioxide.

In addition to iron, smaller amounts of other transitional elements such as vanadium, manganese, chromium, nickel and cobalt can act as magnesium activators and be blended (or milled) into the magnesium. In this aspect of the invention, where a temperature within the disinfection chamber above 100° C. is maintained for several minutes, other metallic reductants such as calcium or sodium amalgam may be used in additional embodiments.

A significant advantage of the chemical combination of the present invention is that it is configured for conditions and situations wherein electrical power is either not available or is of limited availability. For example, the present invention provides a solution to the longstanding problem wherein the transportation of power sources, such as generators, is either difficult or not possible, or wherein the use of fire to generate heat is either not desirable or not possible.

Another important advantage of the present invention is that it solves the problems associated with prior art techniques and methods wherein the transportation of disinfectant chemicals or solutions is difficult due to the bulkiness or large volume and/or weight of such chemicals, solutions and required equipment.

A further advantage of the present invention is that it eliminates the problems related to the transportation of hazardous chemicals that pose health and environmental risks.

Other features and advantages of the present invention will be apparent from the following description in which the preferred embodiments have been set forth in conjunction with the accompanying figures.

BRIEF DESCRIPTION OF THE DRAWINGS

In describing the preferred embodiments of the invention reference will be made to the series of figures briefly described below.

DETAILED DESCRIPTION OF THE PREFERRED EMBODIMENTS

Figure 1:
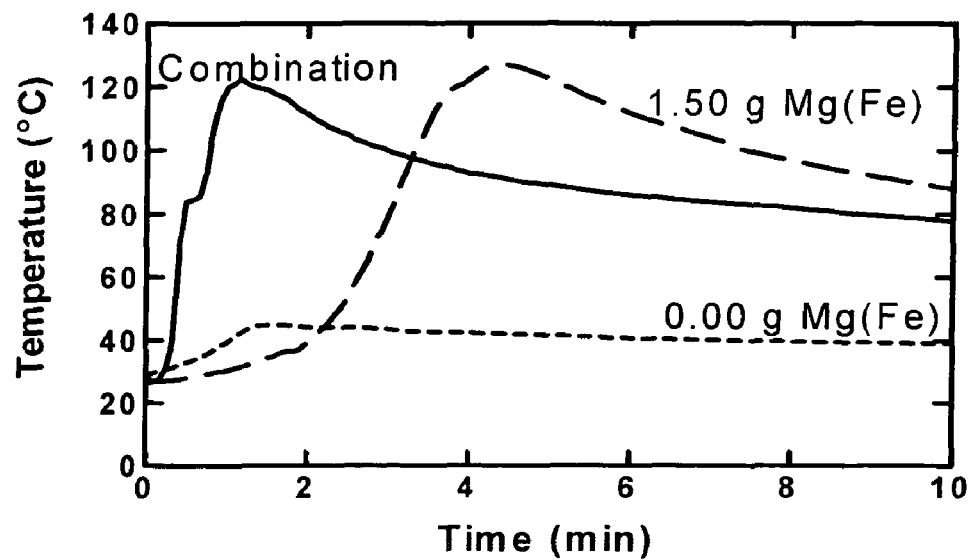
FIG. 1 is a graph that shows the temperature profiles of one embodiment of the chemical combination of the present invention and its individual components.

The present invention is directed toward a chemical combination for use in portable and power-free sanitization, decontamination, disinfection, or sterilization of objects, equipment, or surfaces contaminated with microorganisms or chemical compounds capable of transmitting food-borne illnesses, infections, or disease.

In one embodiment, the chemical combination of the present invention utilizes a metallic reductant comprising magnesium and an iron activator. In another embodiment, the chemical combination of the present invention is magnesium-free. However, in both of the aforementioned embodiments, the chemical combination comprises water or water solutions, a chemical oxidant, a chemical reductant, and an effector.

Thus, in one embodiment, the chemical combination of the present invention comprises water or water solutions, a chemical oxidant, a chemical reductant, an effector and a metallic reductant. The water or water solutions serve as a solvent for the chemical oxidant, the chemical reductant, and the effector, and as a reactant for the metallic reductant. The water or water solutions also serve as a source of steam. The chemical oxidant has the capacity to liberate a biocidal intermediate. The chemical reductant has the capacity to reduce the chemical oxidant. The effector, in less than a stoichiometric amount, induces an electron transfer reaction between the chemical oxidant and the chemical reductant. Reaction of the chemical reductant with the chemical oxidant provides a biocidal intermediate and generates heat and steam. The resulting biocidal intermediate is in the form of a disinfecting solution and gas (or vapor) that can be applied to contaminated surfaces and objects in order to sanitize, decontaminate, disinfect, or sterilize such surfaces, objects, or equipment. The metallic reductant has the capacity to sustainably generate heat and steam. Furthermore, as will be apparent from the ensuing description, when the chemical combination of the present invention is carried out in a closed container, it produces and maintains in said container an environment of disinfecting biocide gas and solution and an atmosphere of steam or of high relative humidity and temperature for a period of time sufficient to destroy all contaminating microorganisms and/or chemicals present.

As explained in the foregoing description, the chemical combination of the present invention uses water or water solutions. One example of a suitable water solution is a salt-water solution. The water or water solution has several functions. Water (or a water solution) stabilizes reducing entities derived from a metallic reductant, such as magnesium, serves as the oxidant of the metallic reductant, and serves as the medium for reactions of dissolved components. Importantly, it serves as a source of steam. For example, when magnesium blended with iron is mixed with an aqueous salt solution, heat is generated in addition to other reactions, and steam evolves.

In accordance with the preferred embodiment of the invention, the chemical oxidant is a halogen-based oxidant. In one embodiment, the halogen-based oxidant is a chlorine-containing compound that has the capacity to liberate chlorine dioxide. In the preferred embodiment, the chlorine-containing compound is sodium, lithium, potassium or any other metal ion salt of chlorite.

In another embodiment, the chemical oxidant is not a chlorine-containing compound, but instead, is a chemically analogous halogen-containing oxidant such as hypobromite, bromite, or bromate, or it is a chalcogen species such as persulfate, or it is hydrogen peroxide. In such an embodiment, exposure of such a chemical oxidant to an appropriate effector such as ascorbate produces reactive potential or actual biocidal intermediates such as bromine dioxide, sulfate radical ion, or hydroxyl radical.

In accordance with the invention, the chemical reductant has a sufficiently high reduction potential to reduce the aforesaid chlorine-containing compound to chloride ion. Thus, in a preferred embodiment, the chemical reductant is a reducing compound or ion chosen from a representative group of such reducing agents, for example, sodium sulfite, sodium dithionite, hypophosphorus acid, iron(II) chloride (ferrous chloride), and mixtures thereof. However, it is to be understood that the chemical reductant can be realized by other suitable and appropriate reducing compounds or ions.

The effector, in less than a stoichiometric amount, induces electron transfer reaction between the chemical oxidant (e.g. chlorine-containing oxidant) and the chemical reductant and makes this reaction kinetically favorable. When the chemical oxidant is a chlorine-containing compound, the effector facilitates reduction of the chemical oxidant to a chloride ion so as to provide a reaction intermediate comprising chlorine dioxide and to generate heat and steam. Specifically, the effector induces the reductant to react with the oxidant by electron transfer thereby accelerating the oxidation-reduction reaction. It has been found that using an ascorbate effector as an inductor of the chlorite-sulfite reaction and combining this reaction with iron-activated magnesium produces a sustainable surge of heat with production of biocidal chlorine dioxide. Thus, in accordance with the invention, the effector is preferably chosen from a representative group consisting of ascorbic acid, erythorbic acid, tartaric acid, or other organic acids, or their respective ions, or a reducing sugar. For example, in the preferred embodiment, the effector is sodium hydrogen ascorbate.

Although the prior art recognizes ascorbate as a reactant, the prior art does not teach, suggest, or recognize the use of ascorbate as an effector. For example, Simpson U.S. Pat. No. 6,440,314 ("Simpson") discloses a technique wherein ascorbic acid is used to remove chlorite from aqueous solution by an oxidation-reduction reaction which produces chloride ion and dehydroascorbic acid. Specifically, Simpson teaches the use of ascorbic acid as a common reactant. Teruo et al. European Patent No. 0196075 ("Teruo") teaches the use of ascorbic acid to accelerate the destruction of chlorite in a contact lens cleaning solution. Teruo treats ascorbic acid as any one of a number of acids used to convert the chlorite ion to chlorous acid which then decomposes. However, neither of these patents teaches, suggests, or recognizes the use of ascorbate as an effector.

In the preferred embodiment, the metallic reductant is magnesium milled or blended with 5 mole percent iron. In one embodiment, this metallic reductant is configured in a form with high surface area (such as powders, turnings, ribbons or wires) which may be provided alone or disbursed in an inert porous matrix and which can further be configured as a flat pad, sphere, a cylinder, a block or irregularly shaped form which permits reaction upon contact with a liquid solvent such as water or water solutions. Such a form of metallic reductant is described in Taub et al. U.S. Pat. No. 5,517,981, the disclosure of which is incorporated herein by reference.

In the preferred embodiment of the chemical combination of the present invention non-zero enthalpic reactions are represented by reactions 1-4.

$$Mg+2H_2O \rightarrow Mg(OH)_2+H_2+352.97 \text{ kJ/mol} \quad (1)$$

$$2Mg+ClO_2^-+4H^+ \rightarrow 2Mg^{2+}+Cl^-+2H_2O+1{,}504.5 \text{ kJ/mol} \quad (2)$$

$$ClO_2^-+2SO_3^{2-} \rightarrow Cl^-+2SO_4^{2-}+648.3 \text{ kJ/mol} \quad (3)$$

$$5ClO_2^-+2H_2O+2.46 \text{ kJ/mol} \rightarrow 4ClO_2+Cl^-+4OH^- \quad (4)$$

In this preferred embodiment, the chemical combination comprises water and the chemical oxidant is the chlorine-containing compound chlorite, the chemical reductant is sulfite, and the metallic reductant is Mg(Fe). The net combination of reactions 1-4 acts to release heat.

The reaction of Mg(Fe) with a salt-water solution produces heat, steam and by-product dihydrogen gas. The chlorite ion suppresses the volume of by-product dihydrogen gas that is released by the reducing action of the metallic reductant Mg(Fe). Chemical additives that can suppress the dihydrogen gas produced by the Mg(Fe)-water chemical reaction include copper(II) chloride, oxyhalogenites, or sodium chlorite ion.

Introduction of sodium hydrogen ascorbate as the effector to the chlorite-sulfite reaction causes acceleration of the chlorite-sulfite reaction such that it becomes a practical source of heat and chlorine dioxide. It has been found that in the absence of an effector that favors electron transfer, the reaction between reductant and oxidant, such as that between sulfite and chlorite ions, is relatively slow. It has also been found that introducing a sodium hydrogen ascorbate effector to the chlorite-sulfite reaction accelerates the chlorite-sulfite reaction when the amount of sodium hydrogen ascorbate is less than a stoichiometric amount. As a result, the accelerated chlorite-sulfite reaction becomes a practical source of heat and chlorine dioxide. Thus, upon transfer of an electron from hydrogen ascorbate ion ($AH^-$) to chlorite ion ($ClO_2^-$), very rapid chemical transformations occur, and the stable but reactive chemical species chlorine dioxide ($.ClO_2$) and chlorine monoxide ($.ClO$) are formed. These species are reactive, because they contain an odd number of electrons. Unlike the chlorite ion, chlorine monoxide readily accepts an electron from the reductant sulfite.

The rapid reaction between chlorite and sulfite that occurs in the presence of the ascorbate effector (i.e. hydrogen ascorbate ion) is represented by the following sequence of reactions:

$$.ClO + SO_3^{2-} \rightarrow ClO^- + SO_3.^- \quad (5)$$

$$ClO_2^- + SO_3.^- \rightarrow .ClO + SO_4^{2-} \quad (6)$$

$$.ClO + ClO_2^- \rightarrow .ClO_2 + ClO^- \quad (7)$$

The prior art clearly does not teach or recognize the novel combination of an oxidation-reduction reaction in the presence of an effector such as hydrogen ascorbate ion (AH$^-$), ascorbic acid (AH$_2$), ascorbate dianion (A$^{2-}$) or erythorbic acid or its respective ions, or tartaric acid, other organic acids and their respective ions or reducing sugars, especially with the purpose of producing a biocidal agent for sanitizing, decontaminating, disinfecting or sterilizing contaminated objects. The oxidation state of chlorine in chlorine dioxide (4+) is relatively higher than that of chlorine in the chlorite ion (3+). However, in accordance with the present invention, an electron of the effector (e.g. hydrogen ascorbate ion) is transferred to the chlorite resulting in a very short-lived transient species which, as a result of further reactions, leads to the production of chlorine dioxide.

The overall reaction between sulfite and chlorite ions is very exothermic. The enthalpy of reaction between sulfite and chlorite ions is approximately −648.3 kJ/mol. In accordance with the invention, the magnesium-water reaction is incorporated with the ascorbate-sulfite-chlorite reaction. Such a feature allows the present invention to be used in various manners. For example, the chemical combination of the present invention can be used in an enclosed device (e.g. autoclave), which is a closed container or pouch constructed of plastics, rubber, aluminum, stainless steel, etc. When the present invention is implemented in an autoclave, sterilization of contaminating microorganisms is accomplished by heating the objects at about 121° C. for an amount of time between about eight and twelve minutes. In order to achieve this temperature with steam, the interior of the autoclave is maintained at a pressure higher than normal atmospheric pressure. Otherwise, steam will maintain the temperature at which liquid water boils, 100° C., at ambient pressures of approximately 1.0 atmosphere (10$^5$ Pascal). Therefore, the present invention functions as a chemical heater which simultaneously releases a powerful disinfectant and heat.

Various experiments and tests were conducted using various embodiments of the invention and are now described in the ensuing description.

Test 1

The novel result of using ascorbate as an effector or activator of a chlorite-sulfite reaction and combining this reaction with iron-activated magnesium results in a sustainable surge of heat with production of biocidal chlorine dioxide. This result is shown in FIG. 1 which shows temperature-time profiles based on the results of an experiment conducted in an adiabatic reactor having a total volume of 100 mL and a reaction volume of 4 mL. The reactant quantities used in the experiment were as follows: 0.75 M sodium chlorite, 0.7 M disodium sulfite, 0.3 M sodium hydrogen ascorbate, and 1.5 g Mg(Fe). A four-fold molar excess of Mg(Fe) over chlorite ion was used. A control experiment with 1.50 mg Mg(Fe) and water alone demonstrates a temperature-time profile with a temperature peak of roughly 122° C. occurring at approximately 4.3 minutes after the start of the reaction. A second type of control test consisting of water, chlorite, sulfite, and ascorbate in water (in the absence of the Mg(Fe) metallic reductant) displays a temperature-time profile with a maximum temperature of roughly 40° C. occurring at approximately 1.3 minutes after the start of the reaction. Combining all of the constituents of the chemical combination in appropriate quantities in the same reaction volume, the present invention shows a temperature-time profile featuring a temperature maximum of ≈120° C. occurring significantly earlier (time≈1.75 minutes) and displaying a more rapid rate of ascent to the maximum than the previously described profiles. Additionally, this reaction composition features the production of a yellow solution and a yellow gas forming concomitantly with the evolution of heat. The yellow gas was collected, isolated, and positively identified by mass spectrometric analysis to be chlorine dioxide (.ClO$_2$).

FIG. 1 shows the heat or temperature profile for (i) the ascorbate-sulfite-chlorite composition without Mg(Fe), (ii) the reaction of Mg(Fe) with water and without the ascorbate-sulfite-chlorite composition, and (iii) the heat or temperature profile when the combination of Mg(Fe) and the ascorbate-sulfite-chlorite composition are combined with water.

As shown by the foregoing description, the chemical combination of the present invention, when using a chlorine-containing compound as the chemical oxidant, reacts to heat a sample of water to temperatures as high as those that are sufficient to destroy contaminating microorganisms. At the same time, it generates quantities of chlorine dioxide as high as those sufficient to destroy contaminating microorganisms, and, in appropriate configurations, sustains the temperature profile of the water and/or generation of biocidal chlorine dioxide for times sufficient to destroy contaminating microorganisms. Thus, the chemical combination generates quantities of chlorine dioxide which, when combined with the heated water, steam and relative humidity, act in concert for sufficient times to destroy contaminating microorganisms. These features and characteristics of the present invention are exemplified by Test 2 and FIG. 2.

Test 2

Figure 2:
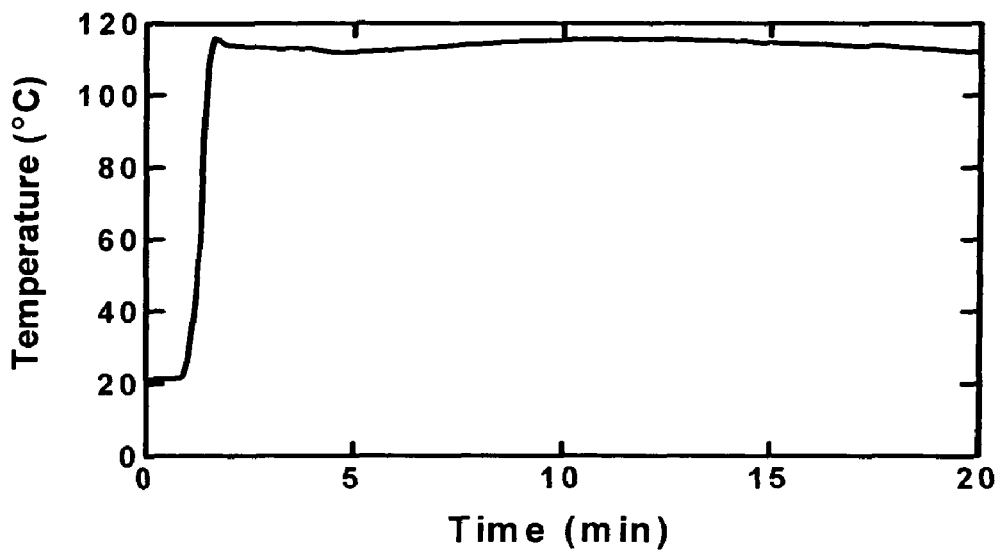
FIG. 2 is a graph that shows a sustainable temperature profile occurring in a 20 L insulated container with a reaction combination comprising water, chlorite, sulfite, ascorbate, and magnesium/iron.

A composition was formed by mixing 3.3 mol Mg(Fe), 0.25 mol ascorbate ion, 1.0 mol sulfite ion, and 1.64 mol chlorite ion in 600 mL of water. As shown in FIG. 2, when this composition is mixed in a relatively larger twenty liter (20 L) insulated container, the higher container-volume-to-surface-area ratio and insulation cause a decrease in heat loss thereby maintaining the maximum temperature for a relatively longer period of time. It was found that maintaining the maximum temperature for a relatively longer period of time enhances both the thermal destruction of contaminating microorganisms and the biocidal efficacy of the resulting chlorine dioxide, since more time is allowed for the generated steam to permeate the surfaces to be decontaminated. As a result, the temperature of the contaminating microorganism is significantly increased which facilitates destruction of the contaminating microorganism, dissolution of chlorine dioxide and contact between the chlorine dioxide and the contaminating microorganisms.

Test 3

A test was conducted to demonstrate the potency of biocidal chlorine dioxide for eliminating the pathogen *Staphylococcus aureus*, whose strains are known to cause foodborne illnesses or infectious diseases. In this test, *S. aureus* cells were suspended in Butterfield's phosphate buffer diluent with a pH of 7.2. The density of each of these robust collections of S. aureus suspensions was approximately $10^7$ colony-forming-units per mL ($10^7$ CFU/mL). For the testing protocol, different suspensions of S. aureus cells were exposed to a single concentration of chlorine dioxide ranging from 0-44 ppm at 30° C. for 3-5 min before diluting and plating on agar. Cell counts were made on samples recovered on Baird-Parker Agar with EY-Tellurite and incubated at 35° C. for 48 hours. Table 1 shows the destruction of S. aureus cultures by addition of aqueous chlorine dioxide solutions. In these test results, S. aureus survival was detected only at the most dilute chlorine dioxide solutions (0.044 ppm). However, increasing the exposure times from a few minutes to 24 hours for the treatment with 0.044 ppm chlorine dioxide solution resulted in 100% inactivation of the pathogens. This observation is consistent with the lethality of chemical agents for destroying microorganisms being the mathematical product of the concentration of the lethal agent (C) and the time (t) of exposure (C×t).

TABLE 1

| [ClO$_2$] (ppm) | CFU/mL ×$10^{-6}$ | Comment |
|---|---|---|
| 0.0 | 9.55 | Control |
| 44 | 0.00 | |
| 0.0 | 3.4 | Control |
| 4.4 | 0.00 | |
| 0.0 | 9.55 | Control |
| 0.44 | 0 | |
| 0.0 | 3.4 | Control |
| 0.044 | 0.116 | 3.4% survivors |
| 0.044 | <1.0 × $10^{-4}$ | Exposure over night |
| 0.044 | 0.00 | Exposure for 24 h |

Test 4

A series of tests was conducted to demonstrate the effectiveness of the novel chemical combination presented in this invention in generating sufficient biocidal chlorine dioxide, heat, and humidity in a closed container to eliminate three different types of microorganisms. The list of microorganisms evaluated in these tests includes vegetative bacterial cells of Listeria monocytogenes and Escherichia coli, and bacterial spores of Bacillus stearothermophilus. In these tests, the chemical composition comprised 186 g sodium chlorite, 126 g disodium sulfite, 50 g sodium hydrogen ascorbate, 24 g iron-activated magnesium powder, and 600 mL of water. The samples comprised microorganisms suspended in Butterfield's phosphate buffer solution in loosely capped test tubes, then placed inside the closed container in which the chemical constituents were mixed. The cells were exposed to the biocidal chlorine dioxide, heat, and humidity generated by the chemical combination for approximately 60 minutes after initiation of the reaction. Table 2 shows that complete destruction of each type of microorganism was achieved by this composition.

TABLE 2

| Species | Initial CFU/mL | Final CFU/mL |
|---|---|---|
| Bacillus stearothermophilus spores | 1.00 × $10^8$ | 0.00 |
| Escherichia coli | 1.20 × $10^7$ | 0.00 |
| Listeria monocytogenes | 1.34 × $10^8$ | 0.00 |

A fraction of the composition used in Test 4 can be successfully employed proportionally if the container size required a smaller amount of the composition. For example, if a container half the size of the original was required, then only 300 mL of water would be used with one-half the weights of each component than the amounts used to conduct Test 4.

As shown by the foregoing description, the chemical combination of the present invention has the capacity to produce and sustain steam, heat and a biocidal intermediate (e.g. chlorine dioxide) so as to achieve an atmosphere that ranges between super-heated steam and a relatively high humidity at sub-boiling temperatures for durations sufficient to effect the destruction of contaminating microorganisms. Such an atmosphere can be achieved in an enclosed container (e.g. autoclave, pouch, plastic, rubber, aluminum or stainless steel containers, etc.) and sustained for an effective amount of time to destroy contaminating microorganisms or biological or chemical agents. Alternatively, the chemical combination of the present invention can be used without any enclosed container. In such a scenario, the heat, steam and biocidal intermediate are generated then distributed over and around objects to be sterilized so as to expose contaminating microorganisms to the steam, heat, and biocidal intermediate.

Thus, the present invention provides a safe, efficient and inexpensive method for chemically generating a biocidal intermediate dissolved in heated water and/or steam which can sanitize, decontaminate, disinfect, and/or sterilize contaminated equipment, objects, or contact surfaces such as field-kitchen equipment, food-preparation surfaces, utensils, mess kits, military equipment and vehicles, weapons, clothing, used surgical instruments, and/or medical equipment. An important feature of the chemical combination of the present invention is its flexibility such that it can be implemented in various ways. As shown in the foregoing description, the chemical combination of the present invention can be carried out in an enclosed device or container (e.g. autoclave, pouch, plastic bag, etc.) and generate sufficient heat, steam, and biocidal intermediate levels to safely sterilize or disinfect contaminated objects within the device in the absence of electrical power or fire. In such circumstances, the chemical combination can generate high temperature of the steam for a sustained duration (e.g. 10-12 minutes) and biocidal intermediate levels in an atmosphere ranging from superheated steam to high relative humidity at sub-boiling temperature that are sufficient to destroy contaminating microorganisms. On the other hand, when an enclosed device is not being used to contain the chemical combination, the heat, steam and biocidal intermediate, whether in gaseous form or in solution, is generated then distributed on, over and around the objects to be decontaminated so as to permeate the contaminated surfaces and objects that must be sterilized and disinfected.

As shown by the foregoing description, the mass (weight) of the chemical combination of the present invention is relatively small requiring a minimum of components and peripheral equipment (e.g. mixing container) thereby allowing the chemical combination to be a lightweight, portable, flexible, safe, easy to transport, and well suited for use in remote field conditions.

The principles, preferred embodiments and modes of operation of the present invention have been described in the foregoing specification. The invention which is intended to be protected herein should not, however, be construed as limited to the particular forms disclosed, as these are to be regarded as illustrative rather than restrictive. Variations and modifications may be made by those skilled in the art without departing from the spirit of the invention. Accordingly, the foregoing detailed description should be considered exemplary in nature and not as limiting the scope and spirit of the invention as set forth in the attached claims.

The invention claimed is:

1. A method of generating a halogen-containing biocidal intermediate for use in the sterilization and disinfection of objects, said method comprising:
    providing a liquid solvent comprising an aqueous solution, such as water or water solutions, having the capacity to function as a source of steam, said liquid solvent being in a range of between about 0.22 mole and about 33.3 moles;
    combining with the liquid solvent a chemical oxidant being in a range of between about 0.003 mole and about 2.1 moles and having the capacity to liberate the halogen-containing biocidal intermediate;
    combining with the liquid solvent a chemical reductant being in a range of between about 0.003 mole and about 1.0 mole and having the capacity to reduce said chemical oxidant; and
    combining with the liquid solvent an electron transfer effector compound being in a range of between about 0.0012 mole and about 0.25 mole and having a capacity to induce electron-transfer reaction chemistry between said chemical oxidant and said chemical reductant and to cause said chemical oxidant to liberate the halogen-containing biocidal intermediate, said effector being an ionic conjugate base form of an organic acid parent compound, with the proviso that said effector excludes the acid form of the parent compound, such that the effector does not contribute protons and does not allow reaction to proceed through acidification;
    wherein the effector initiates a reduction of the oxidant by a transfer of an electron from the oxidant to the effector for causing a release of heat, a decrease in solution pH, and a release of the halogen-containing biocidal intermediate in heated gaseous and aqueous forms, said reaction between the effector and oxidant inducing chemical reaction between the oxidant and reductant for producing heat and increasing solution pH for generating heated halogen-containing biocidal intermediate, with the proviso that said combination excludes an acid for lowering solution pH from near-neutral pH for affecting said objects to expose any contaminating microorganisms to said halogen-containing biocidal intermediate and sterilizing said objects; and wherein said electron-transfer reaction is exothermic and generates heat, said heat sufficient for converting said aqueous solution to steam for further sterilizing said objects.

2. The method according to claim 1 wherein said effector comprises the respective conjugate base ions of an organic acid chosen from the group consisting of ascorbic acid, erythorbic acid, or tartaric acid.

3. The method according to claim 1 wherein said chemical oxidant is chosen from the group consisting of a metal ion salt of a salt of chlorate, hypobromite, bromite, and bromate.

4. The method according to claim 1 wherein the chemical reductant is chosen from the group consisting of sodium sulfite, sodium dithionite, hypophosphorus acid, phosphorus acid, and iron(II).

5. The method-according to claim 1 wherein the halogen-containing biocidal intermediate consists of chlorine dioxide.

6. The method according to claim 1 wherein the liquid solvent is a water solution; the chemical oxidant is the chemical oxidant is chlorite; the chemical reductant is chosen from the group consisting of sodium sulfite, sodium dithionite, hypophosphorus acid, phosphorus acid, and iron(II); and the electron transfer effector is the respective conjugate base ions of an organic acid chosen from the group consisting of ascorbic acid erythorbic acid, and tartaric acid.

7. The method according to claim 1 wherein each step occurs in an enclosed container.

8. The method according to claim 1, further comprising:
    combining with the liquid solvent a metallic reductant and an activator constituent being in a range of between about 0.58 mole and about 3.3 moles and having the capacity to reduce said liquid solvent.

9. The method according to claim 8 wherein said metallic reductant comprises iron-activated magnesium.

10. The method according to claim 8 wherein said activator of the metallic reductant is chosen from the group consisting of V, Cr, Mn, Co, Ni, or any other transitional or more noble metal than magnesium and mixtures thereof.

11. The method according to claim 8 wherein said metallic reductant is configured in a form selected from a group consisting of powder, turnings, ribbons, or wires, said form for reacting upon contact with said liquid solvent having a high surface area.

* * * * *